CHRYSANTHEMUM PLANT

Filed Oct. 30, 1970 2 Sheets-Sheet 1

INVENTORS
WALTER H. JESSEL, JR.,
WILLIAM E. DUFFETT

BY
Oberlin, Maky, Donnelly & Renner
ATTORNEYS

INVENTORS
WALTER H. JESSEL, JR.,
WILLIAM E. DUFFETT
BY
Oberlin, Maky, Donnelly & Renner
ATTORNEYS

United States Patent Office

Plant Pat. 3,263

Patented Dec. 5, 1972

3,263

CHRYSANTHEMUM PLANT

Walter H. Jessel, Jr., Doylestown, and William E. Duffett, Akron, Ohio, assignors to Yoder Brothers, Inc., Barberton, Ohio Filed Oct. 30, 1970, Ser. No. 85,831

Int. Cl. A01h 5/00

U.S. Cl. Plt.—82 1 Claim

The present invention comprises a new and distinct variety of chrysanthemum plant which is a sport of the unpatented but commercially well-known cultivar Torch.

The new cultivar is similar in many respects to Torch, having the same characteristics of:

(1) Growth habit.
(2) Flower size.
(3) Flower form.
(4) Flowering response.

The new cultivar is distinguished from Torch by the following characteristics:

(1) Much more intense red flower color.
(2) Superior color retention under high light and high temperature periods. Although the new cultivar fades somewhat to a lighter red bronze, it still provides a substantially darker overall color than the parent variety Torch which fades under similar conditions to a light orange bronze.

The new cultivar was selected from a flowering plot of the parent variety in Barberton, Ohio, and when asexually reproduced by cuttings at Barberton, Ohio, has been found to retain its distinctive characteristics through successive propagations.

The new variety when grown in the vicinity of Barberton, Ohio, has a response period of approximately 9 weeks. The response time, color, total vigor, and blooming period may vary significantly with varying environmental conditions such as temperature, day length, and light intensity.

Suggested flowering in the United States is all year round.

Figure 1:
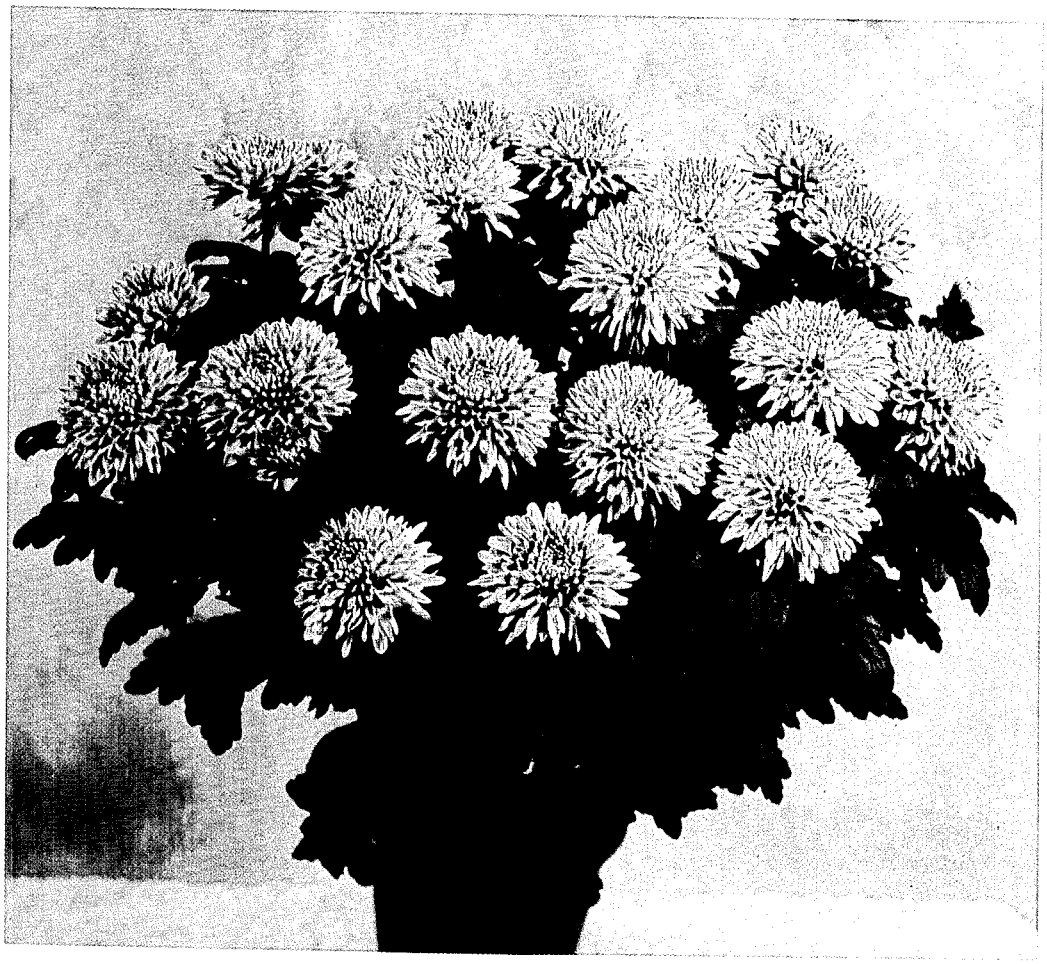
Figure 2:
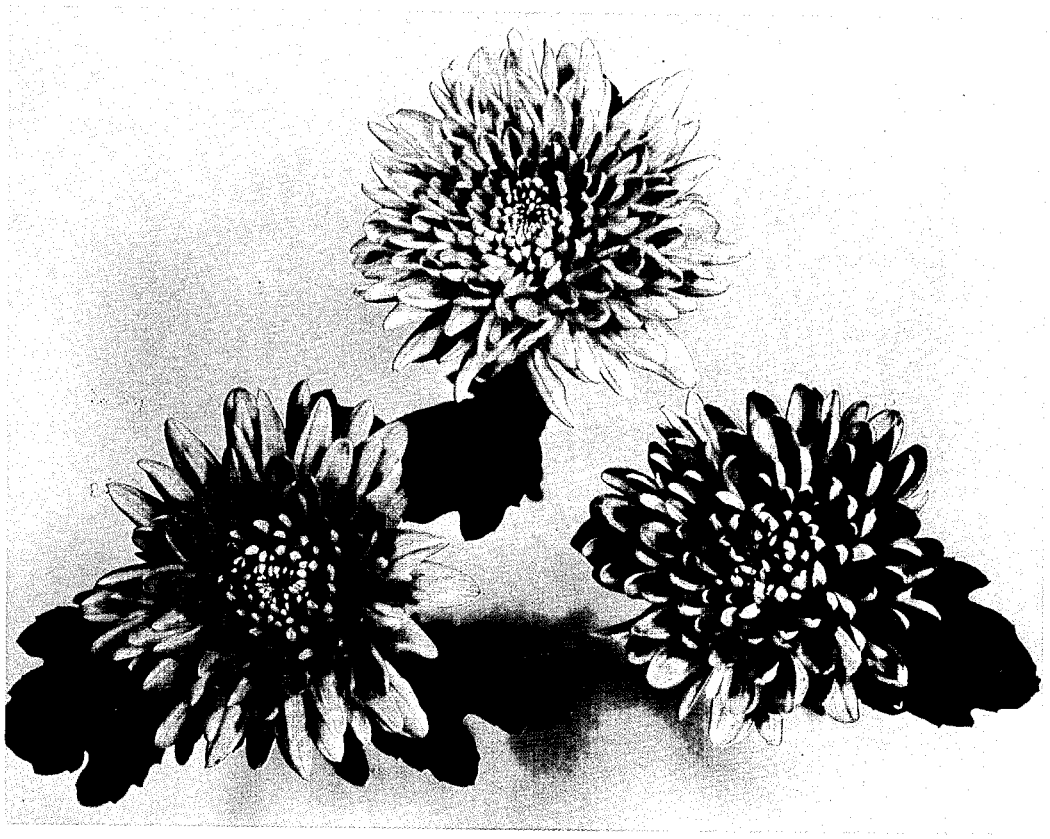

The accompanying drawings show color and form of the new cultivar, with the colors being as nearly true as possible with color illustrations of this type. FIG. 1 shows the new cultivar as a pot mum, with the photograph being taken in a high light, high temperature period. FIG. 2 is an enlarged comparative view of the flowers for the purpose of showing the more intense red flower color of the new cultivar. The flower in the lower left of FIG. 2 is of the new cultivar Red Torch; the flower at center top is of the parent cultivar Torch, and the flower in the lower right of the cultivar Sparkling Mandalay, a cultivar of Yoder Brothers, Inc., assignee of the present invention, which has not as yet been commercially introduced. In FIG. 2, the flower color for both Torch and Red Torch are under cool temperature finishes, thereby accounting for the darker flower color of the new cultivar, as compared with FIG. 1. It should also be noted that the flower of the new cultivar in FIG. 2 is less mature than the flower of Torch, thereby giving the impression of less petal count. However, at full maturity, the petal count and form for both the new and parent cultivars are essentially identical.

The following detailed response information and subsequent data is based on observations made of the new cultivar in a greenhouse in Barberton, Ohio, with color references being made to the Munsell Color Book, 1963 edition, and color comparisons made with the parent cultivar Torch. It should be noted that difficulty was experienced in matching certain of the bronze tones with the color book, and the reference numbers represent the closest available color keys.

Botanical classification: Chrysanthemum morifolium.

Bloom:

*Size.*—3"–3½".
*Fully expanded.*—4".
*Borne.*—Singly on disbudded stem.
*Stems.*—8"–12" long.
*Form.*—Decorative.
*Permanence.*—14 to 16 days.

| | Red Torch | Torch |
|---|---|---|
| Color: | | |
| Center of flower | Maroon red, 7.5R2/8 | Bronze, 10R4/10. |
| Base of petals | do | Do. |
| Inside of petals | Red, 7.5R3/8 to bronze, 10R4/8. | Bronze, 10R4/10 to light bronze, 5YR5/10. |
| Reverse of petals | Light bronze, 7.5YR6/6 | Light bronze. 10YR7/6. |
| Tonality from a distance. | Red | Bronze. |
| Discoloration | Bronze | Light bronze. |

Petals:

*Texture.*—Smooth.
*Appearance and form.*—Sharply keel; taper to point.
*Arrangement.*—Composite, whorled on a single receptacle.
*Persistence.*—Resist shatter.
*Fragrance.*—Typical chrysanthemum.

Reproductive organs:

*Stamen, anthers.*—None to 10.
*Pollen.*—None to very scant.
*Arrangement.*—Clustered in center of flower, if present.
*Styles.*—Present in both ray and disc florets.
*Length.*—Short.
*Ovaries.*—At base of petals attached to receptacle.

Plant:

*Form.*—Herbaceous.
*Growth.*—Upright.
*Height.*—11"–15", depending on culture.
*Spread.*—Very little, approximately 5" as a pinched plant.

Foliage:

*Top side.*—Dark green, 10GY2/4.
*Size.*—4½" long, 2¾" wide.
*Quantity.*—Numerous.
*Shape.*—Palmate.
*Texture.*—Smooth.
*Ribs and veins.*—Prominent.
*Edge*—Indented.
*Serration.*—Moderate.
*Underside.*—Light green, 7.5GY4/4.
*Stipules.*—Rudimentary.

We claim:

1. A new and distinct variety of chrysanthemum characterized particularly as to uniqueness in comparison with the parent cultivar Torch by its more intense red flower color and its superior color retention under high light and high temperature conditions, fading under such conditions to a lighter red bronze as contrasted with the parent cultivar Torch whch fades under such conditions to a light orange bronze.

No references cited.

ROBERT E. BAGWILL, Primary Examiner